United States Patent
Faure et al.

(10) Patent No.: US 8,354,265 B2
(45) Date of Patent: Jan. 15, 2013

(54) CHEMICALS PROMOTING THE GROWTH OF N-ACYLHOMOSERINE LACTONE-DEGRADING BACTERIA

(75) Inventors: Denis Faure, Paris (FR); Amélie Cirou, Les Ulis (FR); Yves Dessaux, Forges-les-Bains (FR)

(73) Assignees: Centre National de la Recherche Scientifique, Paris (FR); Comite Economique Agricole Production des Plants du Nord (Comite Nord Pomme de Terre), Paris (FR)

( * ) Notice: Subject to any disclaimer, the term of this patent is extended or adjusted under 35 U.S.C. 154(b) by 633 days.

(21) Appl. No.: 12/523,095

(22) PCT Filed: Jan. 18, 2008

(86) PCT No.: PCT/IB2008/001156
§ 371 (c)(1),
(2), (4) Date: Oct. 13, 2009

(87) PCT Pub. No.: WO2008/090479
PCT Pub. Date: Jul. 31, 2008

(65) Prior Publication Data
US 2010/0050719 A1 Mar. 4, 2010

Related U.S. Application Data

(60) Provisional application No. 60/885,727, filed on Jan. 19, 2007.

(51) Int. Cl.
C12N 1/20 (2006.01)
C05F 11/08 (2006.01)
C07D 307/02 (2006.01)
C07D 407/00 (2006.01)

(52) U.S. Cl. ............... 435/252.2; 435/252.4; 435/253.3; 435/252.3; 435/252.34; 435/252.31; 71/6; 71/7; 71/8; 71/9; 71/10; 549/295

(58) Field of Classification Search ................ None
See application file for complete search history.

(56) References Cited

U.S. PATENT DOCUMENTS
4,611,069 A * 9/1986 Murib et al. ............... 549/326

FOREIGN PATENT DOCUMENTS
| EP | 1 238 649 A | | 9/2002 |
| KR | 2006032991 A | * | 4/2006 |
| WO | WO 96/29392 A | | 9/1996 |
| WO | WO 2005/056002 A | | 6/2005 |

OTHER PUBLICATIONS

Nunez, M. T. "Efficient Oxidatoin of Phenyl Groups to Carboxylic Acids with Ruthenium Tetraoxide. A Simple Synthesis of (R)-gamma-Caprolactone, the Pheromone of Trogoderma granarium", Journal of Organic Chemistry, 1990, vol. 55, p. 1928-1932.*
English Translation of IDS submitted WO2005056002 provided.*
International Search Report from International Patent Application No. PCT/IB2008/001156, filed Jan. 18, 2008.
Uroz Stphane et al: "Novel bacteria degrading N-acylhomoserine lactones and their use as quenchers of quorum-sensing-regulated functions of plant-pathogenic bacteria"; Microbiology, Society for General Microbiology, Reading, GB; vol. 149, No. Pt. 8; Aug. 1, 2003, pp. 1981-1989; XP02288909.

* cited by examiner

*Primary Examiner* — Jon P Weber
*Assistant Examiner* — Charles Zoltan Constantine
(74) *Attorney, Agent, or Firm* — Alston & Bird LLP

(57) ABSTRACT

The present invention concerns the field of bacterial biocontrol. More precisely, the invention relates to the identification of chemicals which promote the growth of bacteria inactivating NAHL, such as gamma-caprolactone (GCL) and 4-heptanolide (HTN) and their use in soil additives.

6 Claims, 9 Drawing Sheets

CHEMICALS PROMOTING THE GROWTH OF N-ACYLHOMOSERINE LACTONE-DEGRADING BACTERIA

CROSS REFERENCE TO RELATED APPLICATIONS

This application is a national stage application filed under 35 U.S.C. 371 of International Application No. PCT/IB2008/001156, filed Jan. 18, 2008, which claims priority to U.S. Provisional Application No. 60/885,727, filed Jan. 19, 2007.

FIELD AND BACKGROUND OF THE INVENTION

The present invention concerns the field of bacterial biocontrol. More precisely, the invention relates to the identification of chemicals that promote the growth of bacteria inactivating NAHL.

N-acylhomoserine lactones (NAHL) are essential signals for cell-to-cell communication in numerous bacterial populations and communities. The perception of critical concentration of NAHL by bacterial protein sensors (LuxR family) controls the expression of specific genes. The regulatory pathway that links cell quorum to gene expression via the perception of NAHL signal is termed quorum-sensing (QS) (Fuqua et al., 1994). The functions that are regulated through QS are highly diverse (Whitehead et al., 2001), and involve the virulence of animal and plant pathogens, such as *Agrobacterium tumefaciens*, *Erwinia carotovora*, or *Pseudomonas aeruginosa*.

Initially discovered in a few bacteria (Dong et al., 2000; Leadbetter and Greenberg 2000), NAHL-degrading enzymatic activities have now been reported in Proteobacteria belonging to the *Agrobacterium*, *Bosea*, *Commamonas*, *Delftia*, *Pseudomonas*, *Ralstonia*, *Sphingopyxis*, and *Variovorax* genera (Leadbetter and Greenberg, 2000; Huang et al., 2003; Lin et al., 2003; Uroz et al, 2003; Flagan et al., 2003; Hu et al., 2003; Park et al., 2003; d'Angelo-Picard et al., 2005; Jafra et al., 2006), as well as in Actinobacteria and Firmicutes, such as *Arthrobacter*, *Bacillus*, *Rhodococcus* and *Streptomyces* genera (Dong et al., 2000; Lee et al., 2002; Uroz et al., 2003; Park et al., 2003; Park et al., 2005; Park et al., 2006). These NAHL-degrading bacteria were recovered from different environments such as soil, rhizosphere and biofilm. Noticeably, an extensive analysis of the diversity of NAHL-degrading and NAHL-producing bacteria in the rhizosphere of *Nicotiana tabacum* (d'Angelo-Picard et al., 2005) suggests that these two functional communities co-exist in a same environment. Moreover, some bacterial isolates belonging to a same genus (*Agrobacterium*, *Pseudomonas*, *Sphingopyxis*, and *Variovorax*) may be either NAHL producer or degrader. In a few genera, such as *Agrobacterium* and *Pseudomonas*, these two antagonist functions may be co-expressed in a same isolate, and are therefore under a sophisticated regulation, which was explored in the case of *Agrobacterium tumefaciens* (Zhang et al., 2002; Chevrot et al., 2006).

Over past years, antivirulence strategies targeting QS appeared in the literature (Dong et al., 2001; Zhang 2003; Molina et al., 2003; Rasmussen and Givskov, 2006). They include the following approaches:

inhibition of the synthesis of the NAHL signal: for example, triclosan is an antibiotic molecule which inhibits the synthesis of fatty acids, which are themselves necessary to the synthesis of NAHL (Hoang and Schweizer, 1999). However, resistances to this antibiotic appear because it is not specific for the NAHL.

inhibition of the perception of the NAHL signal: NAHL analogues, such as halogenated furanones, can be used to disturb the NAHL signal recognition by the bacterial receptors (Manefield et al., Microbiology. 1999 February; 145 (Pt 2):283-91).

enzymatic degradation of the NAHL signal by genetically modified organisms: recombinant vectors for the expression, in a microorganism or in a transgenic plant, of an exogenous lactonase or acylase, have been proposed (Dong and Zhang, 2005; US 2004/0139495; US 2005/0155088). Transgenic plants expressing an exogenous lactonase, for example encoded by the aiiA gene from *Bacillus* sp., are more resistant to an infection by pathogenic bacteria producing NAHL than their unmodified counterparts. However, this approach is not easy to perform, since it necessitates obtaining transgenic plants.

isolation of NAHL-degrading bacteria, for use as biocontrol agents (Uroz et al., 2003; Jafra et al., 2006) such as bacterial strains belonging to the *Bacillus*, *Rhodococcus* and *Delftia* genera.

In this context, the inventors have investigated whether the metabolic diversity of natural bacterial communities may be engineered to favour NAHL-degrading bacteria through the application of chemicals that promote their growth. As described below, they have demonstrated that NAHL-degrading bacteria may indeed be specifically stimulated, offering a potential strategy for the control of QS-dependent plant pathogens by bacterial population engineering.

According to a first embodiment, the present invention pertains to a soil additive containing at least one compound selected amongst the compounds of formula (I):

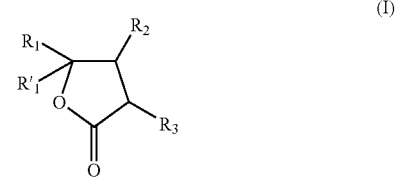

(I)

wherein $R_1$, $R'_1$, $R_2$ and $R_3$ represent a hydrogen atom, a linear or branched $C_1$-$C_{20}$ alkyl group, a linear or branched $C_2$-$C_{20}$ alkylene group carrying one or more double bonds, or a $C_1$-$C_{20}$ alcoxy group, provided that at least one of $R_1$, $R'_1$, $R_2$ and $R_3$ is an alkyl group, an alkylene group or an alcoxy group.

According to a preferred embodiment of the invention, $R_1$, $R'_1$, $R_2$ or $R_3$ represent a linear or branched $C_2$-$C_{14}$, preferably $C_2$-$C_8$ and more preferably $C_2$-$C_6$ alkyl group or a linear or branched $C_2$-$C_{14}$, preferably $C_2$-$C_8$ and more preferably $C_2$-$C_6$ alkylene group carrying one or two double bonds.

In a particular embodiment of the soil additive according to the invention, $R_1$, $R'_1$, $R_2$ or $R_3$ represent an alkyl group or an alkylene group as defined here above, which is substituted with one or more groups selected in the group consisting of hydroxyl, and ketone.

According to another preferred embodiment of the invention, the compound present in the soil additive according to the invention is selected among the following compounds:

compounds in which three of $R_1$, $R'_1$, $R_2$ or $R_3$ are hydrogen atoms and the other one is an alkyl group or an alkylene group; preferably $R_1$ represents an alkyl group of the formula $CH_3$—$(CH_2)_n$— with $1 \leq n \leq 6$.

compounds in which two of $R_1$, $R'_1$, $R_2$ or $R_3$ are hydrogen atoms and each of the other ones is an alkyl group or an alkylene group; preferably $R_1$ represents an alkyl group of formula $CH_3$—$(CH_2)_n$— with $1 \leq n \leq 6$ and $R_2$ represents a methyl group.

compounds in which one of $R_1$, $R'_1$, $R_2$ or $R_3$ is an hydrogen atom and each of the other ones is an alkyl group or an alkylene group; preferably $R_1$ and $R'_1$ represent a methyl group and $R_2$ represents $CH_3$—$CO$—$(CH_2)_2$.

Preferred examples of soil additive according to the invention comprise at least the following compounds:

gamma-caprolactone (GCL) of formula (II):

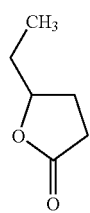

(II)

4-heptanolide (HTN) of formula III:

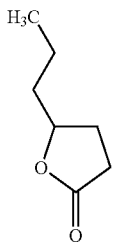

(III)

gamma-octalactone (GOL) of formula IV:

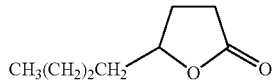

(IV)

4-hydroxy-4-methyl-3-(3-oxobutyl)-valeric acid gamma lactone of formula V:

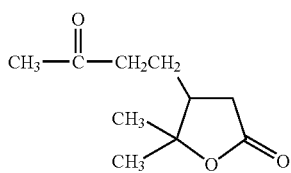

(V)

The soil additive according to the invention preferably contains at least gamma-caprolactone (GCL) or 4-heptanolide (HTN).

In certain situations, the skilled artisan can choose to add, in addition to a compound favouring the growth of NAHL-degrading bacteria, one of several strains of such bacteria. This can be the case, for example, in hydroponic cultures likely to be contaminated by plant pathogens, or in specific soils naturally devoid of NAHL-degrading bacteria. Hence, the present invention also pertains to a soil additive as described above, which further comprises at least one NAHL-degrading bacterial strain, especially a NAHL-degrading bacterial strain, the growth of which is stimulated by gamma-caprolactone (GCL) or 4-heptanolide (HTN). Non-limitative examples of NAHL-degrading bacterial strains that can be used according to this embodiment are bacteria which belong to a genus selected amongst the genera *Delftia, Rhodococcus, Ochrobactrum, Pseudomonas, Rhizobium, Sinorhizobium, Bacillus, Comamonas* and *Variovorax*. Preferred strains which can be incorporated to the soil additives of the invention are *Delftia acidovorans* and *Rhodococcus*, including the bacterial strain *Rhodococcus erythroplis* W2 (Uroz et al., 2003). Of course, several strains can be used in combination.

Another aspect of the present invention is the use of a compound of formula (I):

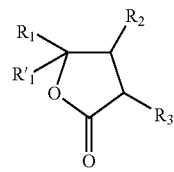

(I)

wherein $R_1$, $R'_1$, $R_2$ and $R_3$ represent a hydrogen atom, a linear or branched $C_1$-$C_{20}$ alkyl group, a linear or branched $C_2$-$C_{20}$ alkylene group carrying one or more double bonds, or a $C_1$-$C_{20}$ alcoxy group provided that at least one of $R_1$, $R'_1$, $R_2$ and $R_3$ is an alkyl group, an alkylene group, or an alcoxy group, for favouring the growth of a NAHL-degrading bacterial strain, in a complex bacterial consortium. Of course, the same particular and preferred compounds as described above for the soil additives are also a part of this aspect of the invention.

In particular, these compounds can be used for preventing biofilm formation and/or for preventing the NAHL-dependent expression of a virulence factor from a pathogenic bacterium in a complex environment. Non-limitative examples of such complex environments which can be treated according to the present invention are a soil, a surface likely to be colonized by bacteria, and the interior of a plumbing material, a pipe, a silo, a fermenter, or a colander.

According to another preferred aspect, the present invention pertains to the use of a soil additive as described above, for protecting plants from biofilm formation and/or from the NAHL-dependent expression of a virulence factor from a pathogenic bacterium. This aspect of the invention can be used for protecting plants either in hydroponic cultures, or in soil cultures. Examples of plant pathogens which can be targeted by the invention are: *Erwinia* sp., especially *Erwinia carotovora* and *Erwinia chrysantemi*, *Burkholderia* sp., especially *Burkholderia cepacia, Burkholderia glumae, Burkholderia plantarii, Agrobacterium tumefaciens, Pantoea sterwartii* and *Ralstonia solanacearum*. Accordingly, non-limitative examples of plants which can benefit from the present invention are: potato plants, tomato plants, lettuce, rice, basil, beet.

A process for determining if a compound is able to stimulate NAHL-degrading bacteria in a bacterial consortium containing at least one *Delftia* strain and/or at least one *Rhodococcus* strain is also part of the present invention. Such a process can comprise the following steps:

(i) incubating a sample of said bacterial consortium in a synthetic medium enriched with said compound to be tested;

(ii) incubating a sample of said bacterial consortium in the same synthetic medium as in (i), but enriched with one of the compounds of formula II-V and preferably with compound of formula II (GCL) or compound of formula III (HTN) in place of said compound to be tested;

(iii) incubating a sample of said bacterial consortium in the same synthetic medium as in (i), without addition of one of the compounds of formula II-V, nor of the compound to be tested; and (iv) after an incubation time of 12 h, preferably of at least 20 h, comparing the ability of each of the consortia obtained in the conditions mentioned in (i), (ii) and (iii) to degrade a NAHL compound such as C6-HSL.

When performing this process, the skilled artisan will consider that the tested compound is able to stimulate NAHL-degrading bacteria if the bacterial consortium obtained in step (i) can degrade said NHL compound as least as efficiently as the bacterial consortium obtained in step (ii). Of course, steps (i) to (iii) can be performed simultaneously or sequentially.

BRIEF DESCRIPTION OF THE DRAWINGS

The invention is further illustrated by the following figures and examples.

EXAMPLES

The experimental data which follow have been obtained by using the materials and methods described below:

Chemicals and Bacterial Media

All chemicals were purchased from Sigma-Aldrich-Fluka. Bacterial rich media were King B (King et al., 1954), Tryptic soy agar (TSA) (AES, France) and TY (0.5% tryptone, 0.3% yeast extract). The minimal medium was AB (Chilton et al., 1974), in which ammonium chloride (1 g/L) was used as a sole nitrogen source and mannitol (2 g/L) as a sole carbon source, excepted when another carbon source is specified. Agar was added at 15 g/L. Fluorescent Pseudomonads were counted under UV (312 nm), on King B agar plates supplemented with ampicillin (40 mg/L) and chloramphenicol (13 mg/L).

Bacterial Enrichment and Isolation from Soils

Figure 1:
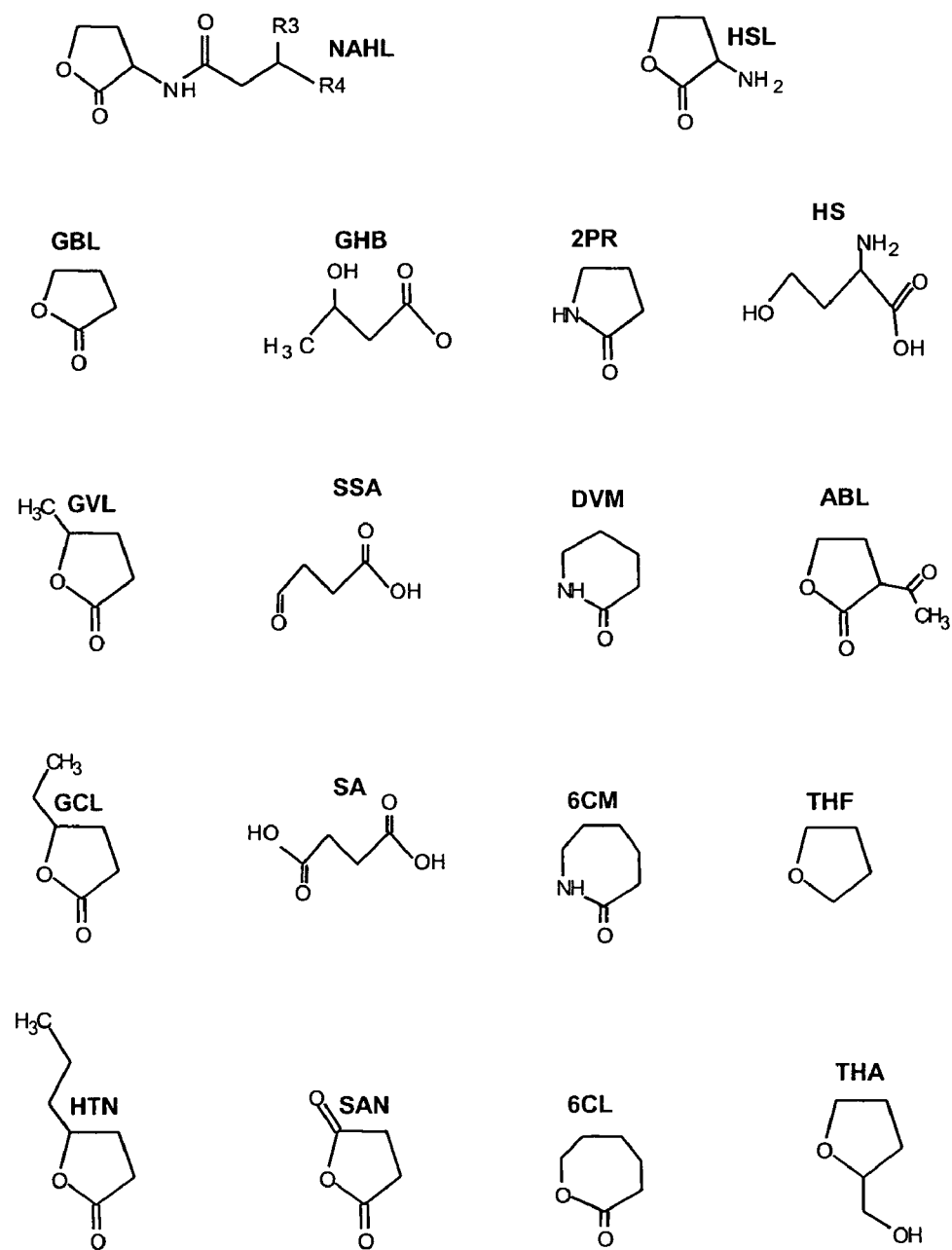
FIG. 1: Structure of a first set of molecules used in this study. Hexanoylhomoserine lactone (C6-HSL) substitutions are as follows: $R_1$ is H and $R_2$ is $CH_2-C_2-CH_3$. The other compounds are homoserine lactone (HSL), gamma-butyrolactone (GBL), gamma-valerolactone (GVL), gamma-caprolactone (GCL), 4-heptanolide (HTN), gamma-hydroxybutyrate (GHB), succinic semialdehyde (SSA), succinic acid (SA), succinic anhydride (SAN), 2-pyrrolidone (2PR), delta-valerolactame (DVM), 6-caprolactame (6CM), 6-caprolactone (6CL), L-homoserine (HS), 2-acetylbutyrolactone (ABL), tetrahydrofurane (THF), tetrahydrofurfuryl alcohol (THA).

Non sterile soil from the CNRS experimental field (Mérantaise) at Gif-sur-Yvette (France) was mixed with sterile sand Loire River and distributed into pots (20 cm in diameter). Some of them were sown with disinfected seeds of Nicotiana tabacum cv. Samson. Pots were randomly placed in the greenhouse (CNRS, Gif-sur-Yvette), under a long day conditions (16 h) at 17° C. (night) and 24° C. (day), and watered daily with tap water. One gram of unplanted or rhizospheric (3-months aged plants) soil was resuspended in 10 mL of sterile 0.8% NaCl. Soil suspensions were diluted (1/50) into AB media supplemented with actidione (100 mg/L) and with mannitol or one of the 17 molecules showed in the FIG. 1. After a 3-days incubation at 25° C. under shaking (180 rpm), the cell cultures were diluted (1/50) into fresh AB media for an additional 2-days enrichment step. At this stage, bacterial consortia were washed twice in NaCl (0.8%), their cell density was adjusted upon OD at 600 nm, and they capacity to inactivate C6-HSL was compared. Bacteria from these consortia were then purified by two successive isolations on AB agar plates supplemented with the corresponding carbon source, and by a third isolation on TY agar plates. Such isolates were tested for NAHL-production and NAHL-degradation.

Bacteria Isolation from Batch Experiments

The non sterile batches (40×60×8 cm) contained 13 L of the nutritive solution Hydrobloom (Cellmax, UK) with Nitrogen at 0.80 g/L, Phosphore at 0.56 g/L and Potassium at 1.48 g/L as major components. The solution was diluted from a concentrated stock solution (×250) with non sterile water from the public water system. One hundred plants of Solanum tuberosum var. Allians, which were recovered from cultures performed under sterile conditions, were placed into holes (3 cm space to each other) of batch covers. Planted batches were placed in the greenhouse (Comité Nord Plants de Pomme de Terre, Bretteville-du-Grand-Caux) under natural light at 10-15° C. (night) and 25-30° C. (day). Four weeks later, 6CL (0.1 mL/L) and GCL (0.1 and 0.4 mL/L) were added (D0), and the bacterial populations were analyzed 14 days (D14) and 28 days (D28) after the beginning of the treatment. An untreated batch was used as a control. One gram of roots (fresh weight) was resuspended in 10 mL of sterile $MgSO_4$ 10 mM, diluted and spread on TSA and King B plates to isolate total cultivable bacteria and fluorescent Pseudomonas, respectively. Three samples were analyzed from each batch at each time D0, D14 and D28; from each sample, thirty isolates from TSA plates and thirty fluorescent isolates from King B plates were individually tested from production and inactivation of NAHL signal.

Identification of NAHL-Producers and NAHL-Degraders

Bacterial isolates grown in 96-microwell plates were individually tested from production of NAHL with the A. tumefaciens biosensor NT1 (pZNLR4) and the inactivation of the C6-HSL signal, as described previously (d'Angelo-Picard et al. 2004). The growth on AB medium with GCL as a sole carbon source was monitored in 96-microwell plates at 600 nm.

rrs Identification and DGGE (Denaturing Gel Gradient Electrophoresis) Analysis

The 5'-end of the rrs gene was amplified with primers pA (5'-AGAGTTTGATCCTGGCTCAG) (SEQ ID NO:1) and 518r (5'-ATTACCGCGGCTGCTGG) (SEQ ID NO:2), and sequenced with pA primer by GenomeExpress (Meylan, France). At least 400 bp were submitted to the NCBI database. Although some sequence comparisons authorized identification of isolates at the species level, only the genus level was retained in this study for homogeneity.

The structure of the bacterial population associated with roots system (ca. 10 g) was analyzed by DGGE of PCR-amplified rrs region (position 341-534 of E. coli sequence). Two samples were analyzed from each batch. The DGGE analysis was performed by Microbial Insights (Rockford, Tenn., USA), as previously described (d'Angelo-Picard et al., 2004). Band positions in each line were converted to 0 (absence) and 1 (presence) value and assembled in a matrix. Profile similarity was calculated with the Dice algorithm using DistAFLP software (http://pbil.univ-lyon1.fr/ADE-4/microb). Sequence identification of selected bands was performed using the sequence match facility of the Ribosomal Database Project (http://rdp.cme.msu.edu/), according to NCBI taxonomy (http://www.ncbi.nlm.nih.gov/Taxonomy/).

Example 1

Enrichment for Bacterial Consortia that Inactivate NAHL Signal

Example 1A

First Set of Compounds

Figure 2:
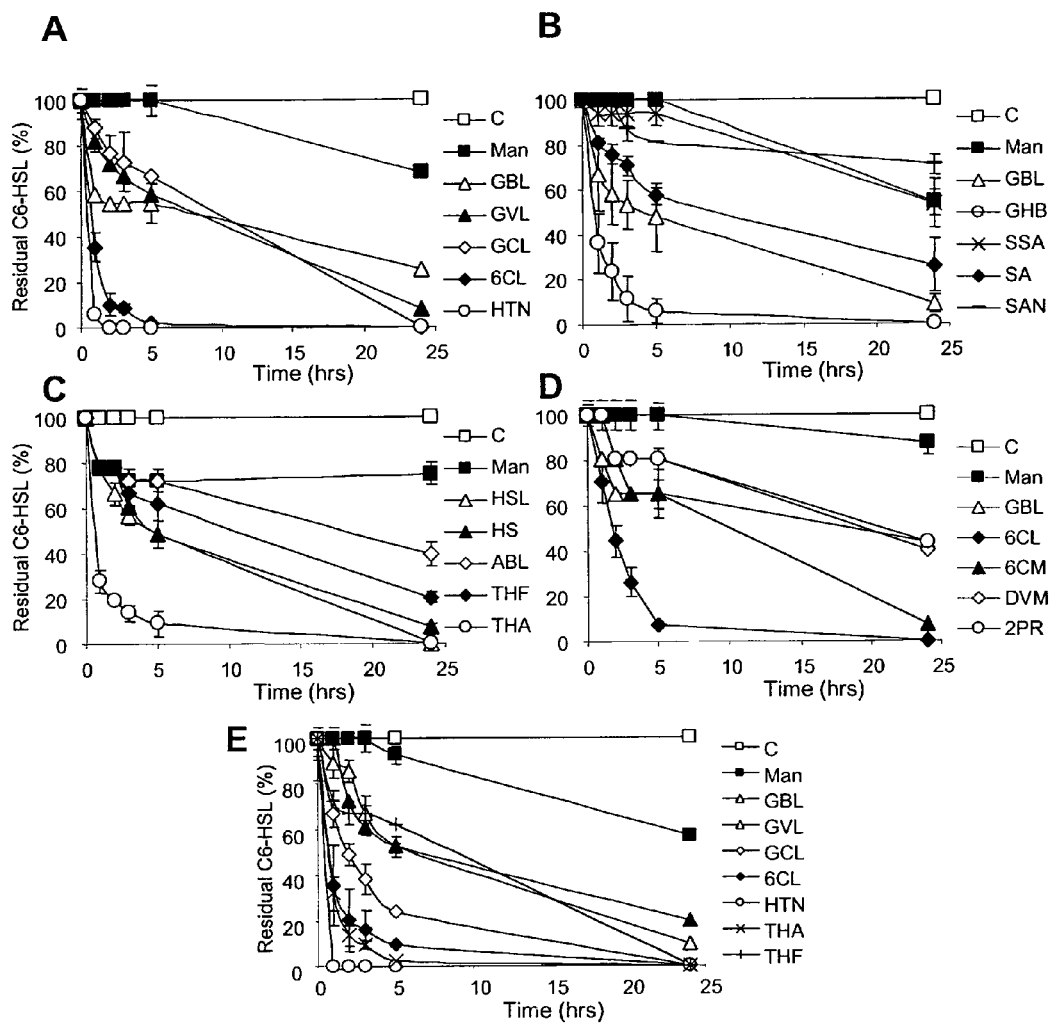
FIG. 2: Kinetics of C6-HSL inactivation by bacterial consortia. The different bacterial consortia, which were obtained after enrichment on the indicated compounds as a sole carbon source (mannitol is abbreviated as Man), were tested for their capacity to inactivate C6-HSL signal (at 25 µM at the beginning of the kinetics). At each point of the kinetics (0, 1, 2, 3, 5 and 24 hours), the uninoculated control (C) was used to estimate the percentage of residual C6-HSL. The kinetics which were simultaneously performed, are showed in a same graph. Bacteria came from unplanted soil (A, B, C, D) and rhizospheric soil (E). The values are the mean of 4 replicates.

Seventeen compounds, which show some structural or metabolic relations with the conserved core of NAHL (FIG. 1), were used individually as a sole carbon source in synthetic medium inoculated with one gram of unplanted soil. After two cycles of enrichment, the resulting bacterial consortia were compared for their capacity to inactivate C6-HSL (FIG. 2 A-D). With the exception of consortia obtained from enrichments on succinic anhydride (SAN) and succinic semialdehyde (SSA), all consortia exhibited a stronger NAHL degrading activity than that of consortia obtained from enrichments performed using mannitol, a sugar analogue structurally unrelated to NAHL. The bacterial consortia that grew on succinic acid (SA), 2-acetylbutyrolactone (ABL), tetrahydrofurane (THF), 6-caprolactame (6CM), delta-valerolactame (DVM), and 2-pyrrolidone (2PR) inactivated from 50 to 80% of the introduced C6-HSL after an incubation time of 24 hours, while over than 90% of C6-HSL signal was obliterated by consortia obtained from enrichments on gamma-butyrolactone (GBL), gamma-hydroxybutyrate (GHB), gamma-valerolactone (GVL), gamma-caprolactone (GCL), 6-caprolactone (6CL), 4-heptanolide (HTN), homoserine lactone (HSL), homoserine (HS) and tetrahydrofurane (THA). Amongst these, the HTN, 6CL, GHB, and THA consortia inactivated more than 90% of the C6-HSL signal after an incubation time of 5 hours. Similar results were observed with bacterial consortia originating from rhizospheric soil (FIG. 2E). In this case, the HTN, THA, 6CL and GCL consortia were the most active towards C6-HSL.

Example 1B

Second Set of Compounds

Figure 3:
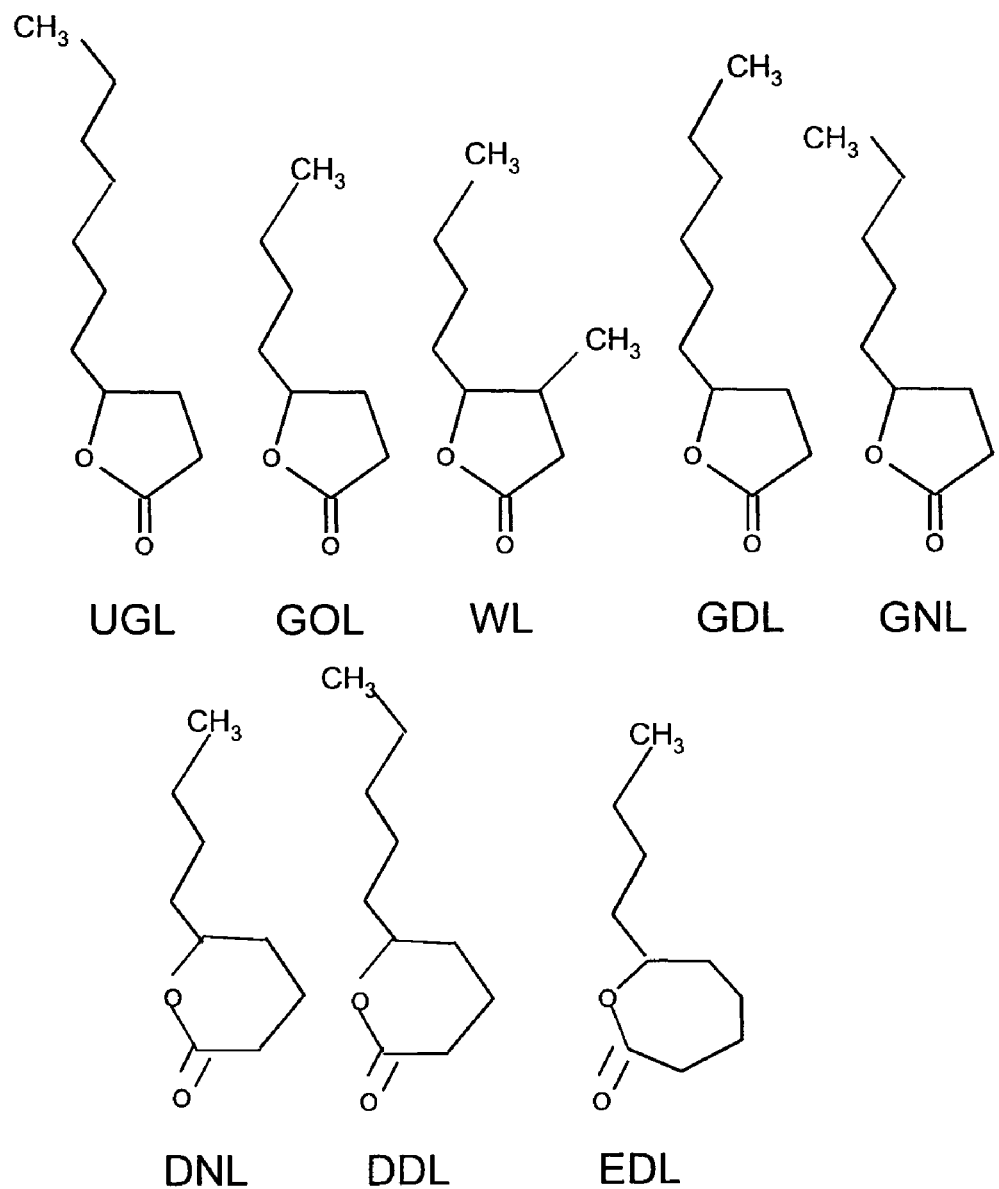
FIG. 3: Structure of a second set of molecules used in this study. Abbreviations: UGL: Undecanoic γ-lactone; GOL: γ-Octalactone; WL: Whiskey lactone; GDL: γ-Decalactone; GNL: γ-Nonalactone; DNL: δ-Nonalactone; DDL: δ-Decalactone; ε-Decalactone.

Additional compounds (FIG. 3) were then individually tested as sole carbon source of soil bacterial consortia, as described above. After two cycles of enrichment, the resulting bacterial consortia were compared for their capacity to inactivate C6-HSL (FIG. 4A) or OC8-HSL (FIG. 4B).

The most efficient compounds for obtaining NAHL-degrading consortia were HTN, GCL and GOL.

Example 2

Structure of the Bacterial Consortia Inactivating NAHL Signal

The bacteria recovered from the mannitol, GBL, GCL, 6CL, HTN, THA, and THF consortia were individually tested for their capacity to produce and inactivate NAHL signals. To this purpose, a collection of 280 isolates which were recovered from 280 independent enrichments (i.e., only one isolate was selected from each of the cultures), was screened for the above two phenotypes. NAHL-producing bacteria were detected among mannitol consortia (10% of the tested strains), as well as GBL (12%), THA (13%) and THF (41%) consortia, while none was present among isolates from GCL, 6CL and HTN consortia. NAHL-inactivating bacteria were recovered from GCL, 6CL, HTN, THA, and THF consortia. GCL, 6CL and HTN consortia showed the higher abundance (40-50%) of NAHL-degrading bacteria. Fifty-three of them were characterized by determining the sequence of the 5' region of their rrs gene. All seventeen isolates from HTN consortia belonged to the *Rhodococcus* genus, while those from 6CL and GCL consortia were related to the *Delftia* (80% of the identified strains), *Chryseobacterium* (10%), *Rhodococcus* (7%), and Ralstonia (3%) genera.

Example 3

Biocontrol Activity of the Bacterial Consortia Against *Erwinia caratovora*

Figure 5:
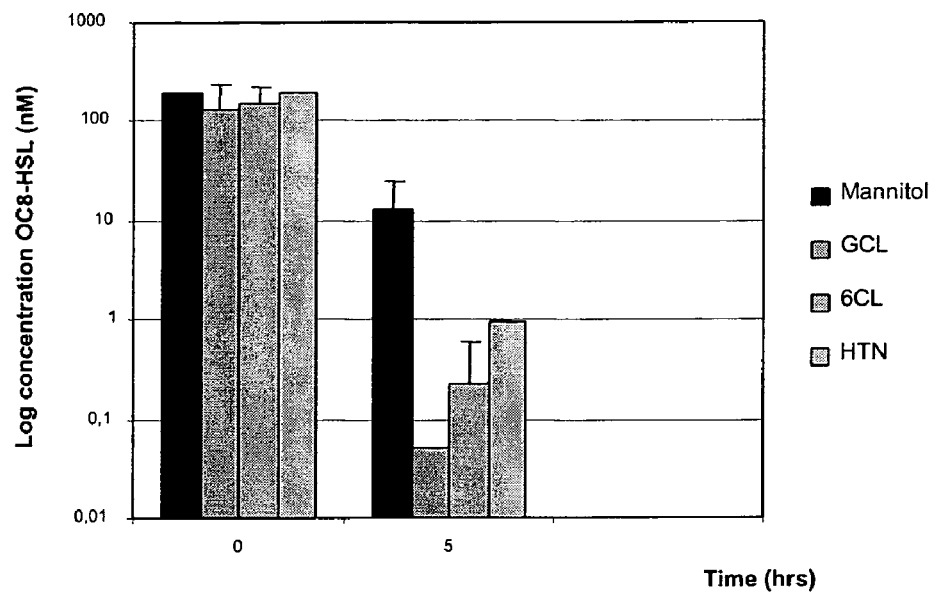
FIG. 5: Inactivation of OC8-HSL by mannitol, 6CL, GCL and HTN consortia.
Figure 6:
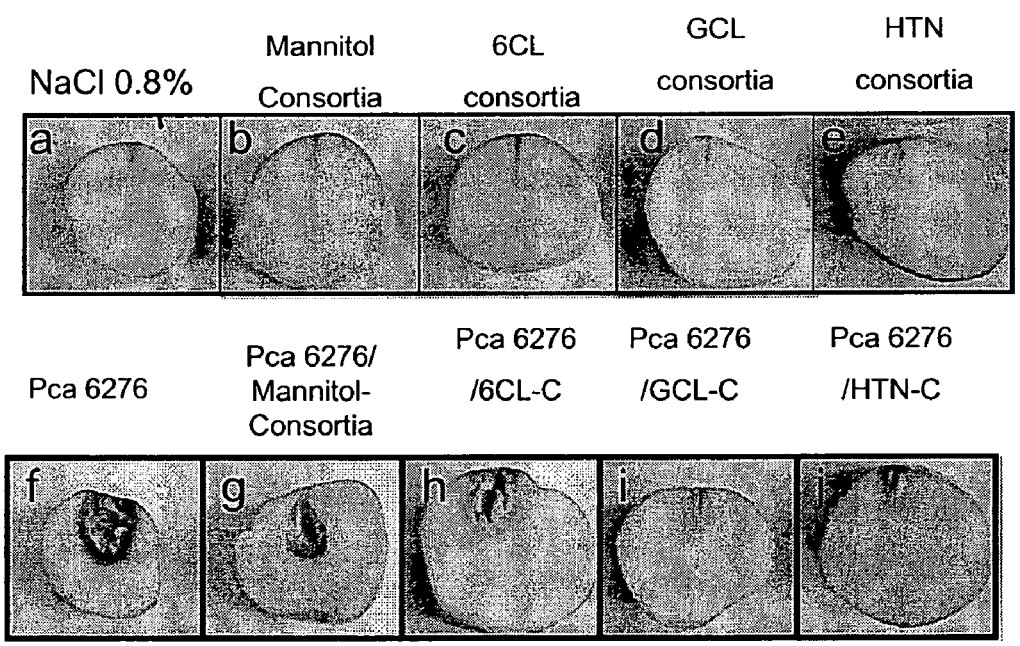
FIG. 6: Maceration assay on potato tubers. Potato tubers were infected by NaCl solution as a negative control (a), or Erwinia carotovora 6276 (f) as a positive control, or bacterial consortia from enrichment procedure in the presence of Mannitol (b), 6CL (c), GCL (d), or HTN (e), or a mix of Erwinia carotovora 6276 and Mannitol (g), 6CL (h), GCL (i), HTN (j) consortia. A biocontrol activity was observed in the presence of the GCL- and HTN-consortia.

The Mannitol-, 6CL-, GCL-, and HTN-consortia were compared for their capacity to inactivated OC8-HSL, the major NAHL produced by the plant pathogen *Erwinia carotovora* subsp. *atroseptica* 6276, as well as for their biocontrol activity against this pathogen in potato maceration assay. In the presence of the 6CL-, GCL-, and HTN-consortia, the C6-HSL and OC8-HSL signals were inactivated more rapidly than in the presence of the Mannitol consortia (FIG. 5). Moreover, the GCL- and HTN-consortia showed biocontrol activity against *E. carotovora* 6276, while the 6CL- and Mannitol-consortia did not (FIG. 6).

Example 4

Growth Stimulation of NAHL-Degrading Bacteria in Hydroponic Plant Cultures

The efficiency of GCL and 6CL and HTN treatments in hydroponic cultures of *Solanum tuberosum* var. Allians was evaluated. The plants were cultivated in vitro under sterile conditions, then placed into batches in a greenhouse at Bretteville-du-Grand-Caux (France) in a non-sterile environment. Especially, a non-sterile nutritive solution was used and served as a source of naturally occurring bacteria. In a first experiment (without plants), two batches of nutritive solution were supplemented with 6CL or GCL (1 mL/L). The ratio of NAHL-degrading bacteria in the nutritive solution was evaluated before the treatment and 14-day later. This percentage increased from 10±2 to 30±2 in the case of the 6CL-treated batch and from 10±2 to 70±2 in the GCL-treated batch. From the 6CL- and GCL-treated batches, 10 NAHL-degrading bacteria were identified by their rrs sequence: 9 belonged to the *Delftia* genus, the other one to the *Rhodococcus* genus.

Because young plants are sensitive to high concentrations (1 mL/L) of GCL and 6CL (data not shown), a second preliminary experiment was conducted in planted batches supplemented with GCL and 6CL (0.1 mL/L). An increase of the ratio of NAHL-degrading bacteria was observed 28 days after the GCL amendment but not after that of 6CL (Table 1). Among the 32 NAHL-degrading bacteria that were characterized by rrs sequencing (Table 1), most of them also belonged to the *Delftia* and *Rhodococcus* genera. At the end of experiment (D28), a higher diversity of NAHL-degrading bacteria would appeared in the untreated batch (7 identified genera) as compared to that observed in the 6CL- and GCL-treated batches (3 identified genera in each batch). Taken together, the results that were obtained with unplanted and planted batches in this set of experiments suggested that GCL supplementation may increase the ratio of NAHL-degrading bacteria, including *Delftia* and *Rhodococcus*, among the bacterial community of potato rhizosphere.

TABLE 1

Level and diversity of NAHL-degrading rhizobacteria after 6CL and GCL treatments. The asterisk indicates that D0 and D28 mean values are statistically different (Student t test; 0.05).

| | Untreated batch | | 6CL (0.1 mL/L) | | GCL (0.1 mL/L) | |
|---|---|---|---|---|---|---|
| | D0 | D28 | D0 | D28 | D0 | D28 |
| Log CFU/gram of root (fresh weight) | 7.8 ± 7.7 | 10.2 ± 9.9 | 8.0 ± 7.6 | 10.5 ± 10.1 | 8.0 ± 7.5 | 10.5 ± 9.8 |
| NAHL producers (%) | 5.6 ± 1.2 | 7.8 ± 1.5 | 7.8 ± 1.2 | 5.6 ± 0.6 | 6.7 ± 1.0 | 11.1 ± 1.5 |
| NAHL degraders (%) | 14.4 ± 3.2 | 13.3 ± 0.1 | 8.9 ± 1.5* | 6.7 ± 1.7* | 16.7 ± 0.1* | 33.3 ± 4.0* |
| rrs-identified NAHL-degraders: | | | | | | |
| *Agrobacterium* | — | 1 | — | 4 | — | — |
| *Bacillus* | — | 1 | — | — | — | 1 |
| *Bosea* | 3 | 1 | — | — | — | — |
| *Delftia* | 3 | 1 | 7 | 2 | 3 | 2 |

TABLE 1-continued

Level and diversity of NAHL-degrading rhizobacteria after 6CL and GCL treatments. The asterisk indicates that D0 and D28 mean values are statistically different (Student t test; 0.05).

|  | Untreated batch | | 6CL (0.1 mL/L) | | GCL (0.1 mL/L) | |
| --- | --- | --- | --- | --- | --- | --- |
|  | D0 | D28 | D0 | D28 | D0 | D28 |
| *Moraxella* | — | 1 | — | — | — | — |
| *Pseudomonas* | 1 | 2 | 1 | 2 | 2 | — |
| *Sphingomonas* | — | 1 | — | — | — | — |
| *Rhodococcus* | 1 | — | — | — | 3 | 5 |
| Total | 8 | 8 | 8 | 8 | 8 | 8 |

Figure 7:
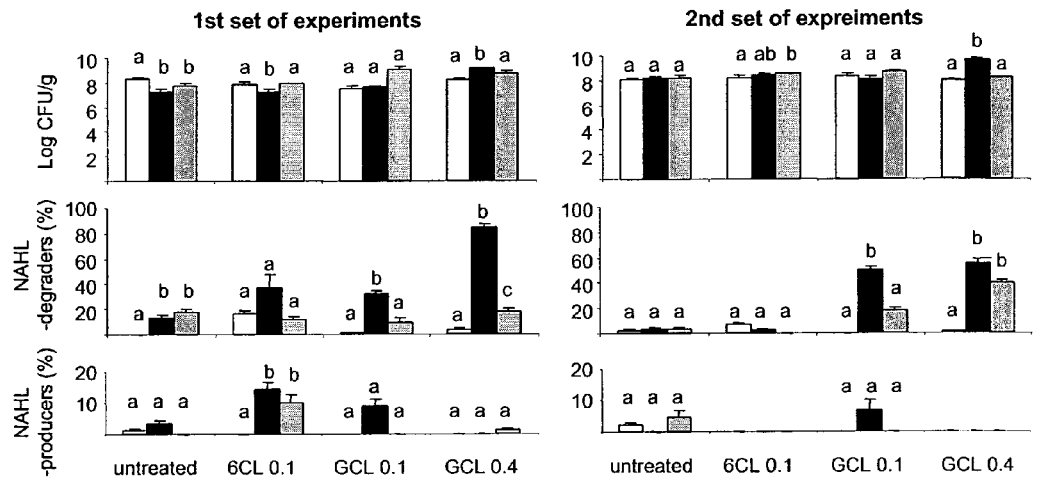
FIG. 7: Percentage of NAHL-degrading and NAHL-producing strains in potato rhizosphere. The percentages of NAHL-degraders and NAHL-producers were estimated among cultivable bacteria (CFU/gram of fresh weight of roots), which were recovered from potato rhizospheres before (D0; white columns), 14 days (D14; black columns) and 28 days (D28; grey columns) after the treatment with GCL or 6CL. An untreated batch was used as a control in the two independent sets of experiments. The mean of three replicates is shown. Statistically different values (Student t test; 0.05) are noted by different letters.

To validate the above preliminary experiments, two extensive and independent analyses of the impact of 6CL and GCL treatments on planted batches were performed under similar conditions in two subsequent sets of experiments. Before (D0) and, at 14 days (D14) and 28 days (D28) following the applications of 6CL (0.1 mL/L) and GCL (0.1 and 0.4 mL/L), the total number of cultivable bacteria was determined, as well as the percentage of NAHL-degrading and NAHL-producing isolates. An untreated batch was used as a control. In the two experiments, cell density (CFU/g of root) consistently increased 14 days after the application of GCL at 0.4 mL/L (FIG. 7). However, no repeatable modification of the ratio of NAHL-producing bacteria was observed. In contrast, an increase of the ratio of NAHL-degrading bacteria was constantly noticed 14 days after GCL (0.1 and 0.4 mL/L) application. In the case of the higher concentration of GCL, such an increase was still observed 28 days after the treatment in both experiments. In the untreated and 6CL-treated batches, the proportion of NAHL-degrading bacteria remained at a quite similar level during all experiments, suggesting that, to the contrary of GCL, 6CL had a no specific effect on the NAHL-degrading bacteria of the investigated rhizosphere.

Figure 8:
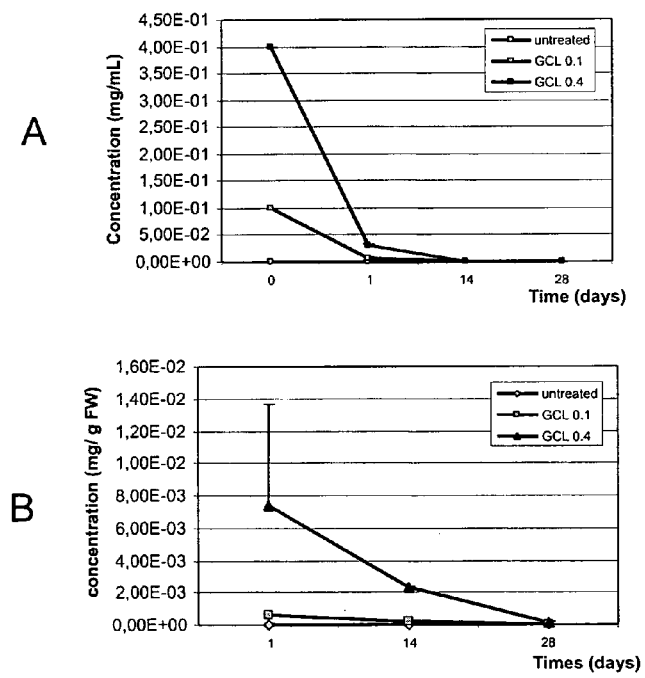
FIG. 8: Concentration of GCL in hydroponic solution (A) and plant tissues (B) of hydroponic cultures of potato plants.

In the case of the GCL assay, the level of GCL in untreated and treated batches in both hydroponic solution and plant tissues was evaluated by HPLC-MS analysis. The GCL rapidly decreased in the course of the time (FIG. 8). Fourteen days after the application of GCL, the GCL concentration in hydroponic solution was lower than $10^{-5}$ mg/mL, which is the lowest detectable concentration of GCL in this assay. In untreated plant tissues, GCL was detected at a low level, from 2 to $4.10^{-5}$ mg/mL. Twenty-eight days after the application of GCL, the GCL concentration was similar in both treated and untreated samples.

Figure 9:
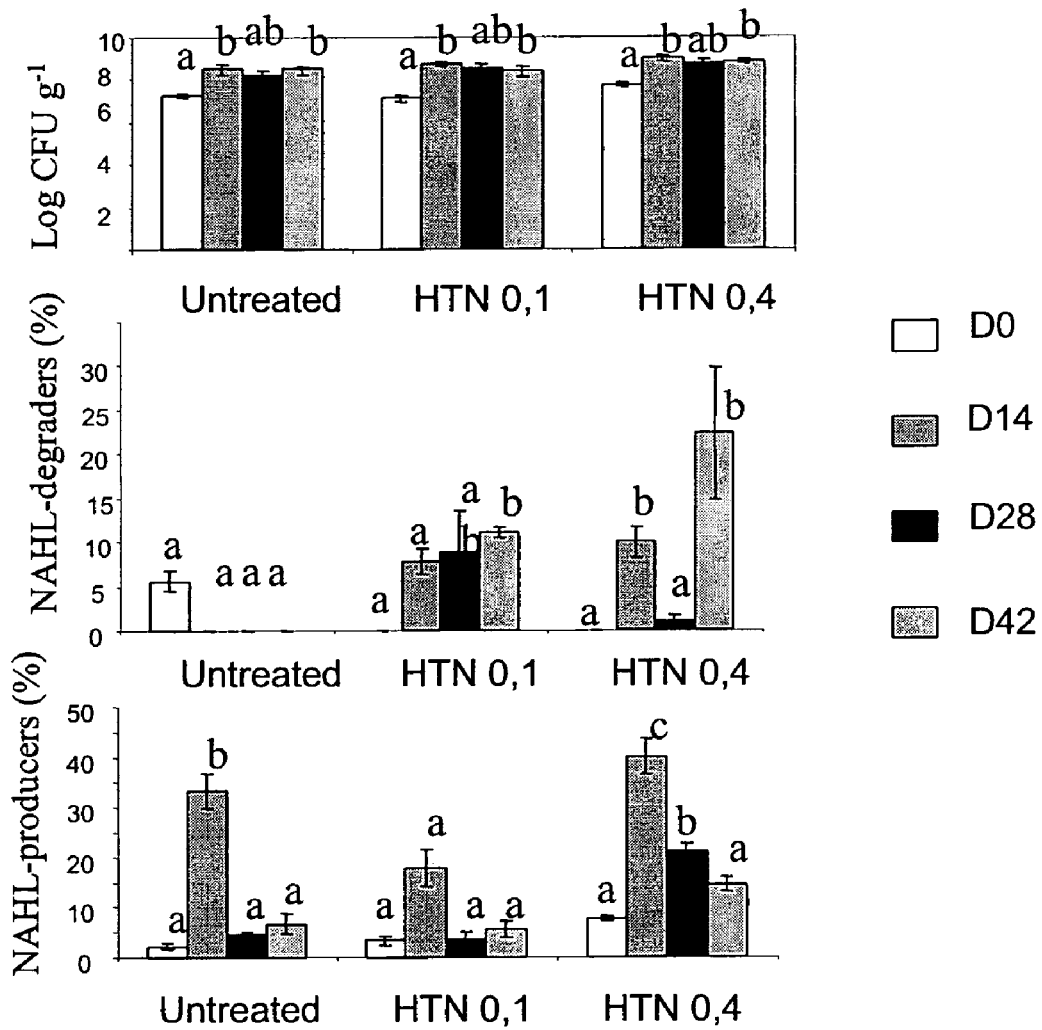
FIG. 9: Percentage of NAHL-degrading and NAHL-producing strains in potato rhizosphere after treatment with HTN. The percentage of NAHL degraders and NAHL producers was estimated among cultivable bacteria (cfu/g of fresh weight of roots), which were recovered from potato rhizospheres before the treatment (D0; white columns), 14 days (D14; dark grey columns), 28 days (D28; black columns) after the first treatment and 42 days after the first treatment, i.e., 14 days after the second treatment (D42; grey columns). The letters indicate statistically different values (Student's t-test; 0.05).

An additional experiment was conducted to determine the impact of HTN (0.1 and 0.4 mL/L) treatment on planted batches, under the same conditions as described above. In this experiment, a second treatment was performed 28 days after the first treatment, and the total number of cultivable bacteria, as well as the percentage of NAHL-degrading and NAHL-producing isolates were determined 14 days after this treatment, i.e., 42 days after the first treatment (D42). This assay confirmed the ability of HTN to stimulate the growth of NAHL-degrading bacteria (FIG. 9).

Example 5

NAHL-Inactivation and Assimilation of GCL are Partly Linked

The above observation prompted the evaluation of the hypothesis of a metabolic link between the ability to assimilate GCL as a sole carbon source and the capacity to inactivate NAHL. Among the collected isolates from the untreated and GCL-treated batches (at D14 and D28), the capability of bacteria to assimilate GCL as a sole carbon source was determined strain by strain. Results were cross-examined with respect to the ability of each strain to inactivate (or not) NAHL signal. From this analysis (FIG. 10), four categories of bacterial isolates emerged: bacteria that do neither assimilate GCL, nor inactivate NAHL signal; those only inactivating NAHL signal; those only assimilating GCL; and those both assimilating GCL and inactivating NAHL. The later group was only detected in the treated batches, in which all but a few of the NAHL-degrading bacteria were also GCL-assimilating bacteria. A link between assimilation of GCL and NAHL-inactivation was therefore established.

Example 6

Diversity of the NAHL-Degrading and GCL-Assimilating Bacteria

The impact of GCL and 6CL on the diversity of NAHL-degrading strains was assessed by comparing 262 NAHL-degrading strains sampled from the two first sets of experiments, at the beginning of the experiments (D0) and after 14 and 28 days. The isolates were identified by rrs-sequencing (Table 2). At D0, most of the NAHL-degrading isolates were identified as *Delftia*. However, at D14 and D28, the *Agrobacterium* isolates dominated in untreated batches, while they were not detected in the treated batches. In those, the more frequently counted bacteria were *Delftia* and *Rhodococcus*. All these *Delftia* and *Rhodococcus* isolates grew on GCL as a sole carbon source. However, sixteen isolates which assimilated GCL and did not inactivate NAHL signal (FIG. 10), were identified as *Acidovorax* (7 isolates), *Microbacterium* (3), *Pseudomonas* (2), *Azospirillum* (1), *Staphylococcus* (1), *Flavobacterium* (1), and *Achromobacter* (1).

TABLE 2

Diversity of NAHL-degrading rhizobacteria after 6CL and GCL treatments

|  | Two first sets of experiments | | | | |
| --- | --- | --- | --- | --- | --- |
|  | D0 | D14 and D28 | | | |
|  | All batches | Untreated | 6CL 0.1 | GCL 0.1 | GCL 0.4 |
| rrs-identified NAHL-degraders: | 28 | 30 | 18 | 80 | 106 |
| *Agrobacterium* | 4 | 19 | — | — | — |
| *Delftia* | 19 | 3 | 9 | 16 | 9 |

TABLE 2-continued

Diversity of NAHL-degrading rhizobacteria after 6CL and GCL treatments

|  | Two first sets of experiments | | | |
|---|---|---|---|---|
|  | D0 | D14 and D28 | | |
|  | All batches | Untreated | 6CL 0.1 | GCL 0.1 | GCL 0.4 |
| Pseudomonas | 1 | 1 | — | 1 | 1 |
| Rhizobium | 3 | — | 1 | 1 | — |
| Rhodococcus | — | 6 | 6 | 60 | 96 |
| Others | 1 | 1 | 2 | 2 | — |

To analyze the impact of HTN on the diversity of NAHL-degrading strains, 50 NAHL-degrading strains were sampled from the third set of experiments, at the beginning of the experiments (D0) and after 14 and 42 days. The isolates were identified by rrs-sequencing (Table 3). At D0, all of the 5 NAHL-degrading isolates analyzed were identified as *Agrobacterium*. However, at D14 and D42, the *Rhodococcus* isolates dominated in treated batches, in which *Delftia* and *Sinorhizobium* were also detected

TABLE 3

Diversity of NAHL-degrading rhizobacteria after HTN treatments

|  | D 0 All batches | D 14 and D 42 | | |
|---|---|---|---|---|
|  |  | Untreated | HTN 0.1 | HTN 0.4 |
| rrs-identified NAHL-degraders: | 5 | 0 | 17 | 28 |
| Agrobacterium | 5 | — | — | — |
| Delftia | — | — | 1 | — |
| Sinorhizobium | — | — | — | 1 |
| Rhodococcus | — | — | 16 | 27 |

Example 7

Impact of GCL and 6CL on Other Bacterial Groups

Figure 10:
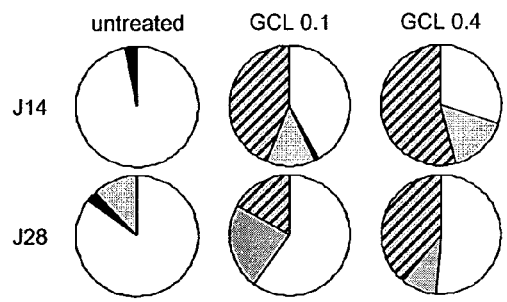
FIG. 10: Assimilation of GCL and NAHL-degrading capacity. Each disk represents 90 isolates from untreated or GCL-treated (0.1 and 0.4 mL/L) batches 14 days (D14) and 28 days (D28) after the beginning of the treatment. Pieces indicate the proportion of bacteria which assimilated GCL as a sole carbon source and inactivate C6-HSL signal (hatched), those which only assimilated GCL (grey), those which only inactivate NAHL signal (black), and those which did not assimilate GCL, nor inactivated NAHL signal (white).
Figure 11:
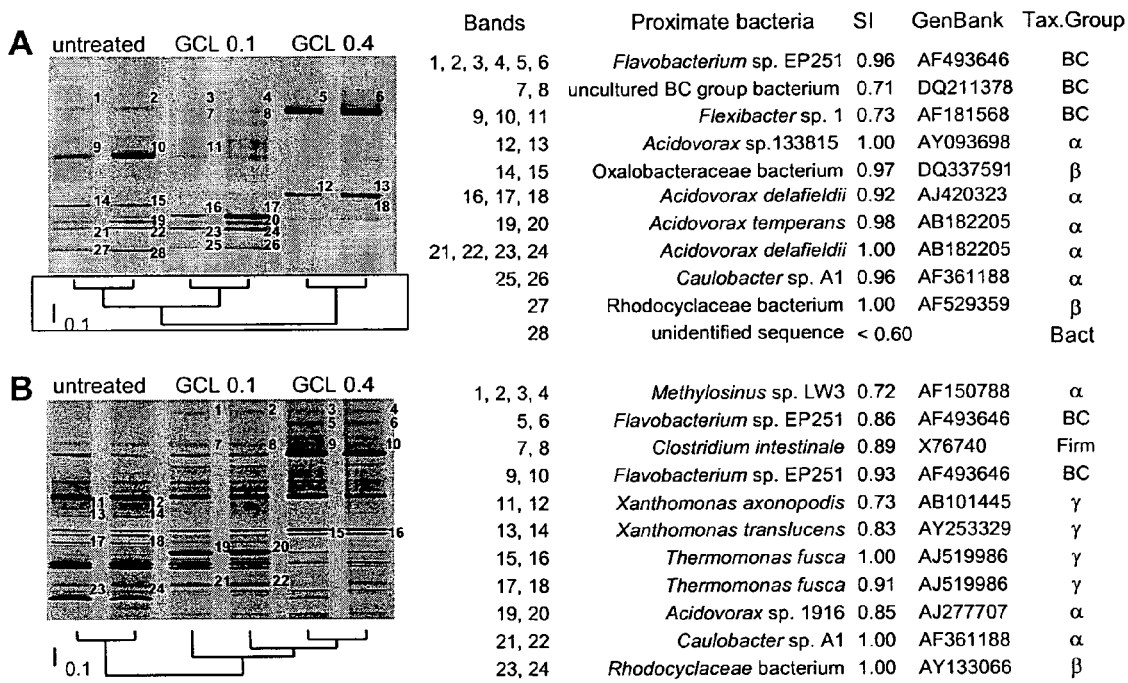
FIG. 11: DGGE analyses. DGGE analyses were performed on two samples from a same batch, 14 days (panel A) and 28 days (panel B) after the application of GCL (0.1 and 0.4 mL/L). Numbered bands on pictures were analyzed by sequencing. For each sequence or group of sequences, one of the closest rrs sequences was indicated. It is identified by its Genbank number, the similarity indice (SI) (calculated at Ribosomal Database Project http://rdp.cme.msu.edu/), and the name and taxonomical position of the bacteria of origin (Bact, Bacteria; BC, Bacteroidetes/Chlorobi group; Firm, Firmicutes; α,α-proteobacteria; β,β-proteobacteria; and γ,γ-proteobacteria).

In addition to the above data that deal with cultivable bacteria, DGGE analyses were performed on D14 and D28 samples (GCL-treated and untreated batches) from the second set of experiments mentioned above. This approach revealed a drastic remodelling of bacterial populations after GCL application (FIG. 11). Such modifications were most visible in the presence of the highest concentration of GCL (0.4 mL/L). Some identified bands were more intense, or only present, in the batch treated with GCL at 0.4 mL/L. The nucleotide sequence of these bands was related to the *Flavobacterium, Acidovorax, Thermomonas* genera. Some others bands were more intense—or only present—in the untreated batch. In this case, they were generated from bacteria close to *Flexibacter, Acidovorax, Xanthomonas, Thermomonas* genera and to an uncharacterized Rhodocyclaceae bacterium. Some different bands, which were related to *Thermomonas* and *Acidovorax* genera, were absent or present in untreated and GCL-treated samples. This feature suggests a fine modification of the structure of bacterial populations at sub-genus level. Remarkably, the rrs-sequences belonging to *Acidovorax* and *Flavobacterium* genera were identified among the bacteria which assimilated GCL and did not inactivate NAHL-signal (FIG. 10), as well as among the DGGE bands that appeared in the batch treated with GCL (FIG. 11).

Example 8

Figure 12:
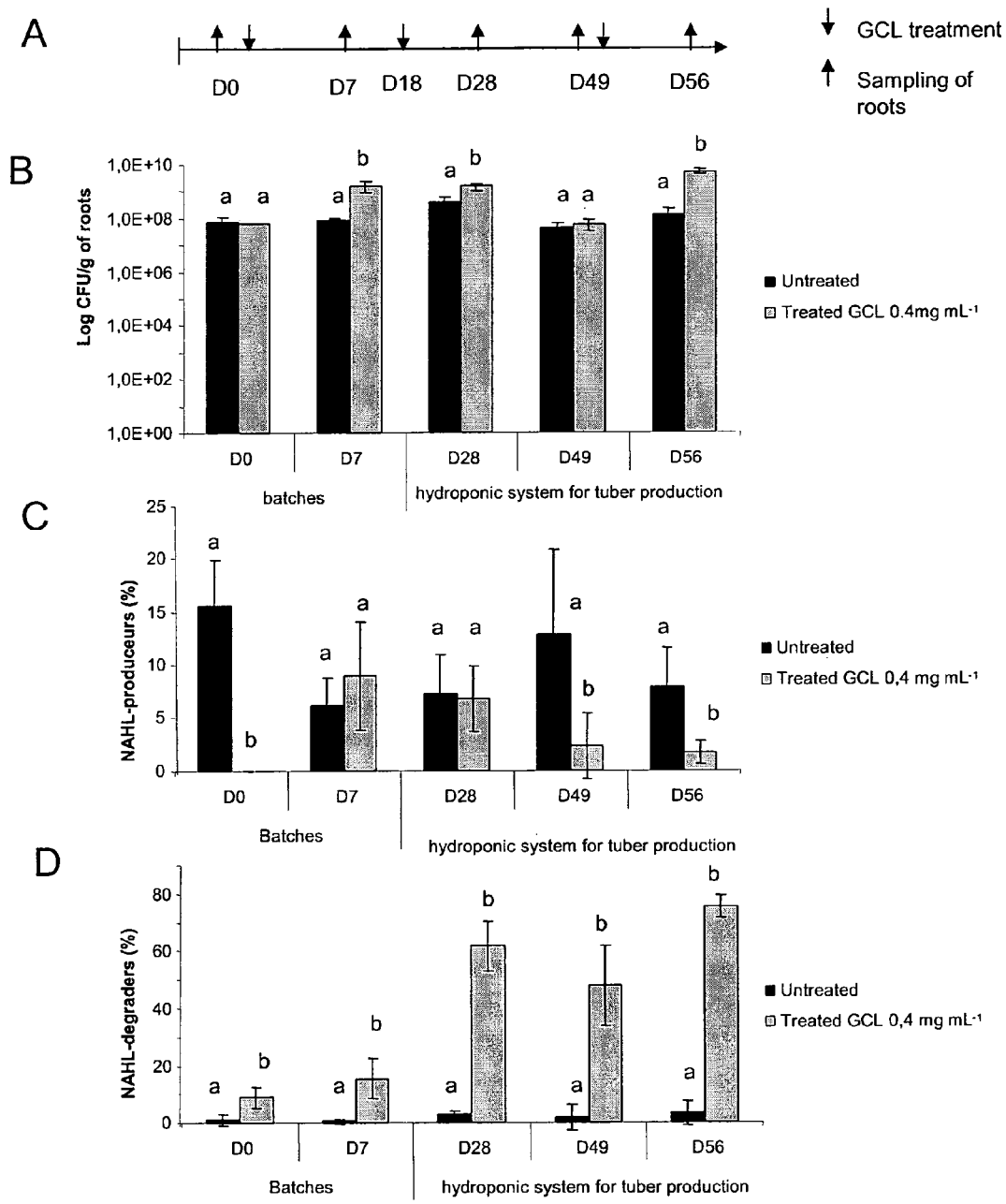
FIG. 12: Impact of GCL (0.4 mg/mL) treatment on potato plants culture in greenhouse during 56 days. The time scale (A) indicates the different GCL treatments (at day-0, day-18 and day-49) and the analyses of rhizospheric samples (day-0 before treatment, day-7, day-28, day-49 and day-56). The plants were cultivated in hydroponic batches from D0 to D17, then transferred into hydroponic system allowing the long term culture until tuberisation. At each time, three samples (D0 and D7) and four samples (D28, D49 and D56) were analyzed: the number of CFU/g of roots was estimated (B), as well as the percentage of acyl-HSL-producing (C) and acyl-HSL degrading strains. Different letters indicate a significative difference (Student's t-test; α=0.05) between the two conditions, untreated and GCL-treated.

Impact of GCL Treatment on Potato Plants Culture in Hydroponic System Allowing the Long-Term Culture Potato plants cultured in greenhouse were treated with GCL (0.4 mg m/L) at D0, D18 and D49, and rhizospheric samples were analyzed at D0 (before treatment), D7, D28, D49 and D56. The plants were cultivated in hydroponic batches from D0 to D17, then transferred into hydroponic system allowing the long term culture until tuberisation. FIG. 12 shows a clear effect of GCL treatment on the percentage of acyl-HSL degraders at D28, D49 and D56.

Discussion on the Above Examples

Bacteria that inactivate NAHL signal are taxonomically diverse ($\alpha$-, $\beta$-, $\gamma$-proteobacteria, Firmicutes, and Actinobacteria) and may represent 5 to 15% of total cultivable bacteria in the rhizospheric soils (d'Angelo-Picard et al., 2004; d'Angelo-Picard et al., 2005), as well as in hydroponic plant cultures (FIG. 7). The NAHL-degrading bacteria were proposed to play a role in the modulation of quorum-sensing communication in planta (Chevrot et al., 2006), as well as to obliterate the antibiotic activity assigned to NAHL-derived compounds (Kaufmann et al., 2005). In addition, these bacteria constitute potential biocontrol agents permitting to protect plants from the NAHL-dependent expression of some virulence factors from several pathogens such as Erwinia (Uroz et al., 2003; Dong et al., 2004). This study demonstrates that the application of degradable chemicals might be a valuable tool to stimulate the growth of NAHL-degrading bacteria and therefore increase the percentage of such bacteria in the rhizosphere of hydroponic cultures of *Solanum tuberosum*.

Figure 4:
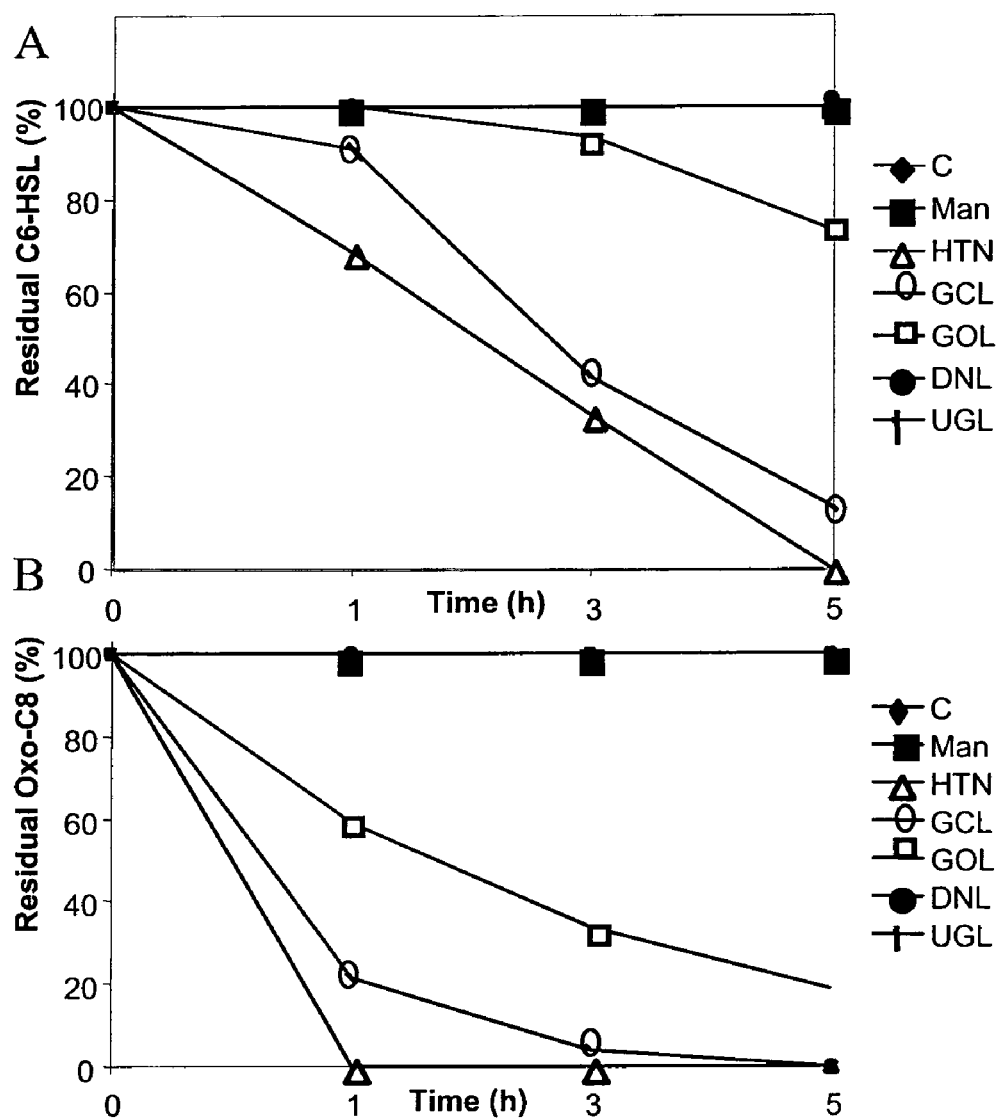
FIG. 4: Kinetics of NAHL inactivation by bacterial consortia. (A) NAHL is C6-HSL with an initial concentration of 25 µM (B) NAHL is 3-oxo-octanoylhomoserine lactone (OC8-HSL), with an initial concentration of 200 nM. The different bacterial consortia obtained after enrichment on the indicated compounds as a sole carbon source (mannitol is abbreviated as Man) were tested to for their capacity to inactivate NAHL signal. At each time (0, 1, 3 and 5 hrs), the uninoculated control (C) was used to estimate the percentage of residual NAHL.

Among 25 assayed molecules (FIGS. 1 and 3) structurally related to the conserved core of NAHL, GCL, 6CL, HTN and GOL stimulated the growth of NAHL-degrading bacteria after enrichment procedures from soil and rhizospheric samples (FIGS. 2 and 4). Moreover, when GCL or HTN was applied to hydroponic plant cultures, a significant increase of the percentage of NAHL-degrading bacteria among total cultivable bacteria was observed (FIGS. 7 and 9). Most of these bacteria, the growth of which was stimulated, were also able to use GCL as a sole carbon source (FIG. 10). They belong to the *Rhodococcus* and *Delftia* genera, most probably to the *Rhodococcus erythropolis* and *Delftia acidovorans* species (Tables 2 and 3), as suggested by the partial sequence of their rrs gene. Interestingly, isolates of these two species were already known to inactivate NAHL signals. In the case of *Delftia* genus, little is known about the enzymatic properties that are required for NAHL inactivation (Jafra et al., 2006); only two rrs partial sequences of NAHL-degrading strains A207 and A317 were deposited in Genbank (AY580081 and AY581676) by S. Jafra, P. Garbeva and J. M. Van der Wolf. In contrast, the NAHL-degrading strains of *Rhodococcus* genus are of a particular interest (Uroz et al., 2003; Park et al., 2006), because they can modify the structure of NAHL by at least three enzymatic activities: a lactonase that opens the GBL-ring of NAHL (Park et al., 2006); an acylase that releases HS and a fatty acid, and an oxidoreductase that reduces the 3-oxo substitution to an hydroxyl on some NAHL (Uroz et al., 2003; Uroz et al., 2005).

A more unexpected effect of the GCL application is the stimulation of the growth of a restricted number of NAHL-degrading species, especially *Rhodococcus erythropolis* and *Delftia acidovorans*, as evaluated in front of the wide diversity of NAHL-degrading bacteria in the soil and rhizosphere (α-, β-, γ-proteobacteria, Firmicutes, and Actinobacteria). These two species emerged after application of GCL in two distinct environments, soil and hydroponic cultures. The efficiency of the GCL application could therefore be dependent upon the natural occurrence of these two species in the amended environments. Besides, in natural environments from where *Rhodococcus* and *Delftia* are absent, the inoculation of selected isolates of these genera appears feasible. However, *Rhodococcus erythropolis* and *Delftia acidovorans* are very common in soils and rhizosphere, including soils in which pesticides (such as 2,4-dichlorophenoxyacetate), halogenated compounds, and oil pollutants were introduced (Muller et al., 2001; Uroz et al., 2003; Hamamura et al., 2006). Whether these xenobiotics increase the emergence of NAHL-degrading bacteria in such environments remains open to investigation.

In addition to a significant stimulation of the growth of some *Rhodococcus* and *Delftia* strains, a decrease of the percentage of *A. tumefaciens* isolates among the NAHL-degrading rhizobacteria was observed (Table 2). This feature suggests that both the level and diversity of NAHL-degrading bacteria was modified after GCL-treatments. In contrast, no modification of level of NAHL-degrading bacteria was noticed among fluorescent Pseudomonads which represent about 10% of the cultivable bacteria in the rhizosphere of hydroponic culture of *Solanum tuberosum*. DGGE analysis also revealed significant modifications of the structure of bacterial communities in GCL-treated batches (FIG. 11). The identified genera the growth of which was stimulated by GCL applications were close to the *Flavobacterium*, *Acidovorax*, *Thermomonas*. However, the capacity of all these DGGE-indentified bacteria to hydrolyze GCL and/or NAHL could not be predicted, and some bacterial isolates, which assimilated GCL and did not inactivate NAHL-signal (FIG. 10), were identified after rrs-sequencing as *Acidovorax* and *Flavobacterium*. Bacteria assimilating GCL, but inactive towards NAHL, are amongst the most undesirable bacteria as they disturb the effect of GCL as a stimulator of the growth of NAHL-degrading bacteria.

REFERENCES

Chevrot R., Rosen R., Haudecoeur E., Cirou A., Shelp B. J., Ron E., and Faure D. (2006) GABA controls the level of quorum-sensing signal in *Agrobacterium tumefaciens*. *Proc Natl Acad Sci USA* 103: 7460-7464.

Chilton M., Currier T C., Farrand S K., Bendich A J., Gordon M P., Nester E W. (1974) *Agrobacterium tumefaciens* DNA and PS8 bacteriophage DNA not detected in crown gall tumors. *Proc Natl Acad Sci USA* 71:3672-3676.

d'Angelo-Picard, C., Faure D., Carlier, A., Uroz, S., Raffoux, A., Fray, R. and Dessaux, Y. (2004) Dynamics of bacterial populations in the rhizosphere of tobacco plants producing—or not—the quorum sensing signals hexanoyl- and 3-oxo-hexanoyl-homoserine lactone. *FEMS Microbiol Ecol* 51: 19-29.

d'Angelo-Picard, C., Faure D., Penot, I. and Dessaux, Y. (2005) Diversity of N-acylhomoserine lactone-producing and -degrading bacteria in soil and tobacco rhizosphere. *Environ Microbiol* 7: 1796-1808.

Dong, Y. H., Xu, J. L., Li, X. Z., and Zhang, L. H. (2000) AiiA, an enzyme that inactivates the acylhomoserine lactone quorum-sensing signal and attenuates the virulence of *Erwinia carotovora*. *Proc Natl Acad Sci USA* 97: 3526-3531.

Dong, Y. H., Wang, L. H., Xu, J. L., Zhang, H. B., Zhang, X. F., and Zhang, L. H. (2001) Quenching quorum-sensing-dependent bacterial infection by an N-acyl homoserine lactonase. *Nature* 411: 813-817.

Dong, Y H, Zhang, X F, Xu, J L, and Zhang, L H. (2004) Insecticidal *Bacillus thuringiensis* silences *Erwinia carotovora* virulence by a new form of microbial antagonism, signal interference. *Appl Environ Microbiol* 70:954-60.

Dong Y H and Zhang L H. (2005) Quorum sensing and quorum-quenching enzymes. *J Microbiol*. February; 43 Spec No:101-9.

Flagan, S., Ching, W. K., and Leadbetter, J. R. (2003) *Arthrobacter* strain VAI-A utilizes acyl-homoserine lactone inactivation products and stimulates quorum signal biodegradation by *Variovorax paradoxus*. *Appl Environ Microbiol* 69: 909-916.

Fuqua, W. C., Winans, S. C., and Greenberg, E. P. (1994) Quorum sensing in bacteria: the LuxR/LuxI family of cell density-responsive transcriptional regulators. *J. Bacteriol*. 176: 269-275.

Hamamura, N., Olson, S. H., Ward, D. M., and Inskeep, W. P. (2006) Microbial population dynamics associated with crude-oil biodegradation in diverse soils. *Appl Environ Microbiol* 72: 6316-24.

Hoang T T and Schweizer H P. (1999) Characterization of *Pseudomonas aeruginosa* enoyl-acyl carrier protein reductase (FabI): a target for the antimicrobial triclosan and its role in acylated homoserine lactone synthesis. *J Bacteriol*. 181(17):5489-97.

Hu, J. Y., Fan, Y., Lin, Y. H., Zhang, H. B., Ong, S. L., Dong, N., Xu, J. L., Ng, W. J., and Zhang, L. H. (2003) Microbial diversity and prevalence of virulent pathogens in biofilms developed in a water reclamation system. *Res Microbiol* 154: 623-629.

Huang, J. J., Han, J. I., Zhang, L. H., and Leadbetter, J. R. (2003) Utilization of acyl-homoserine lactone quorum signals for growth by a soil pseudomonad and *Pseudomonas aeruginosa* PAO1. *Appl Environ Microbiol* 69: 5941-5949.

Jafra S, Przysowa J, Czajkowski R, Michta A, Garbeva P, Van der Wolf J M. (2006) Detection and characterization of bacteria from the potato rhizosphere degrading N-acyl-homoserine lactone. *Can J Microbiol*. October; 52(10): 1006-1015.

Kaufmann, G. F., Sartorio, R., Lee, S. H., Rogers, C. J., Meijler, M. M., Moss, J. A., Clapham, B., Brogan, A. P., Dickerson, T. J., and Janda, K. D. (2005) Revisiting quorum sensing: discovery of additional chemical and biological functions for 3-oxo-N-acylhomoserine lactones. *Proc Natl Acad Sci USA* 102: 309-314.

King, E. O., Ward, M. K., and Raney, D. E. (1954) Two simple media for the demonstration of pyocyanin and fluorescin. *J Lab Clin Med* 44:301-307.

Kluepfel, D. A. (1993) The behavior and tracking of bacteria in the rhizosphere, *Annu Rev Phytopathol* 31: 441-472.

Leadbetter, J. R., and Greenberg, E. P. (2000) Metabolism of acyl-homoserine lactone quorum-sensing signals by *Variovorax paradoxus*. *J Bacteriol* 182: 6921-6926.

Lee, S. J., Park, S. Y., Lee, J. J., Yum, D. Y., Koo, B. T., and Lee, J. K. (2002) Genes encoding the N-acyl homoserine lactone-degrading enzyme are widespread in many subspecies of *Bacillus thuringiensis*. *Appl Environ Microbiol* 68: 3919-3924.

Lemanceau, P., and Alabouvette, C. (1993) Suppression of *fusarium* wilts by fluorescent pseudomonads: mechanisms and applications. *Biocontrol Science and Technology* 3: 219-234.

Lin, Y. H., Xu, J. L., Hu, J., Wang, L. H., Ong, S. L., Leadbetter, J. R., and Zhang, L. H. (2003) Acyl-homoserine lactone acylase from *Ralstonia* strain XJ12B represents a novel and potent class of quorum-quenching enzymes. *Mol Microbiol* 47: 849-860.

Manefield M, de Nys R, Kumar N, Read R, Givskov M, Steinberg P, Kjelleberg S. (1999) Evidence that halogenated furanones from *Delisea pulchra* inhibit acylated homoserine lactone (AHL)-mediated gene expression by displacing the AHL signal from its receptor protein. *Microbiology*. February; 145 (Pt 2): 283-91.

Molina, L., Constantinescu, F., Michel, L., Reimmann, C., Duffy, B., and Défago, G. (2003) Degradation of pathogen quorum-sensing molecules by soil bacteria: a preventive and curative biological control mechanism. *FEMS Microbiol Ecol* 1522: 1-11.

Muller, R. H., Kleinsteuber, S., and Babel, W. (2001) Physiological and genetic characteristics of two bacterial strains utilizing phenoxypropionate and phenoxyacetate herbicides. *Microbiol. Res.* 156:121-31.

Park, S. Y., Lee, S. J., Oh, T. K., Oh, J. W., Koo, B. T., Yum, D. Y., and Lee, J. K. (2003) AhlD, an N-acylhomoserine lactonase in *Arthrobacter* sp., and predicted homologues in other bacteria. *Microbiology* 149: 1541-1550.

Park, S. Y., Kang, H. O., Jang, H. S., Lee, J. K., Koo, B. T., and Yum, D. Y. (2005) Identification of extracellular N-acylhomoserine lactone acylase from a *Streptomyces* sp. and its application to quorum quenching. *Appl Environ Microbiol* 71: 2632-2641.

Park, S. Y., Hwang, B. J., Shin, M. H., Kim, J. A., Kim, H. K., and Lee, J. K. (2006) N-acylhomoserine lactonase-producing *Rhodococcus* spp. with different AHL-degrading activities. *FEMS Microbiol Lett* 261: 102-108.

Rasmussen, T. B., Givskov, M. (2006) Quorum-sensing inhibitors as anti-pathogenic drugs. *Int J Med Microbiol* 296: 149-161.

Uroz, S., d'Angelo-Picard, C., Carlier, A., Elasri, M., Sicot, C., Petit, A., Oger, P., Faure, D., and Dessaux, Y. (2003) Novel bacteria degrading N-acylhomoserine lactones and their use as quenchers of quorum-sensing-regulated functions of plant-pathogenic bacteria. *Microbiology* 149: 1981-1989.

Uroz S., Chhabra S. R., Camara M., Williams P., Oger P. and Dessaux Y. (2005) N-acylhomoserine lactone quorum-sensing molecules are modified and degraded by *Rhodococcus erythropolis* W2 by both amidolytic and novel oxidoreductase activities. *Microbiology* 151: 3313-3322.

Weller, D. M. (1988) Biological control of soilborne plant pathogens in the rhizosphere with bacteria. *Annu Rev Phytopathol* 26: 379-407

Whitehead, N. A., Barnard, A. M., Slater, H., Simpson, N. J., and Salmond, G. P. C. (2001) Quorum-sensing in Gram-negative bacteria. *FEMS Microbiol Rev* 25: 365-404.

Zhang, L. H. (2003) Quorum-quenching and proactive host defense. *Trends Plant Sci* 8: 238-244.

Zhang, H. B., Wang, L. H., and Zhang, L. H. (2002) Genetic control of quorum-sensing signal turnover in *Agrobacterium tumefaciens*. *Proc Natl Acad Sci USA* 99: 4638-4643.

---

The invention claimed is:

1. A soil additive, comprising at least one compound selected in the group consisting of gamma-caprolactone (GCL) and 4-heptanolide (HTN), and at least one NAHL-degrading bacterial strain, wherein the growth of said NAHL-degrading bacterial strain is stimulated by said compound.

2. The soil additive of claim 1, wherein said bacterial strain is selected in the group consisting of *Delftia, Rhodococcus, Pseudomonas, Rhizobium* and *Sinorhizobium*.

3. The soil additive of claim 1, which comprises at least one *Delftia acidovorans* strain and at least one *Rhodococcus erythroplis* strain.

4. The soil additive of claim 1, which comprises at least one *Delftia acidovorans* strain or at least one *Rhodococcus erythroplis* strain.

5. The soil additive of claim 1, which comprises at least one *Delftia acidovorans* strain.

6. The soil additive of claim 1, which comprises at least one *Rhodococcus erythroplis* strain.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
agagtttgat cctggctcag                   20

<210> SEQ ID NO 2
<211> LENGTH: 17
<212> TYPE: DNA
<213> ORGANISM: Artificial
<220> FEATURE:
<223> OTHER INFORMATION: primer

<400> SEQUENCE: 2
attaccgcgg ctgctgg                      17